(12) United States Patent
Lee

(10) Patent No.: US 10,076,280 B2
(45) Date of Patent: Sep. 18, 2018

(54) BONE-CONDUCTIVE AROUSAL INDUCTION APPARATUS

(71) Applicant: Choon Kee Lee, Denver, CO (US)

(72) Inventor: Choon Kee Lee, Denver, CO (US)

(*) Notice: Subject to any disclaimer, the term of this patent is extended or adjusted under 35 U.S.C. 154(b) by 455 days.

(21) Appl. No.: 14/870,865

(22) Filed: Sep. 30, 2015

(65) Prior Publication Data

US 2017/0087050 A1    Mar. 30, 2017

(51) Int. Cl.
*A61B 5/00* (2006.01)
*A61B 5/1455* (2006.01)
*A61B 5/08* (2006.01)
*A61B 5/113* (2006.01)
*A61F 5/56* (2006.01)

(52) U.S. Cl.
CPC .......... *A61B 5/6814* (2013.01); *A61B 5/0051* (2013.01); *A61B 5/0826* (2013.01); *A61B 5/113* (2013.01); *A61B 5/14552* (2013.01); *A61B 5/4806* (2013.01); *A61B 5/4815* (2013.01); *A61B 5/4836* (2013.01); *A61F 5/56* (2013.01); *A61B 5/4818* (2013.01); *A61B 5/6833* (2013.01); *A61B 2560/0412* (2013.01)

(58) Field of Classification Search
CPC ....... A61F 5/56; A61B 5/0051; A61B 5/0826; A61B 5/4806; A61B 5/4815; A61B 5/4818; A61B 5/6814
USPC ......................................................... 128/848
See application file for complete search history.

(56) References Cited

U.S. PATENT DOCUMENTS

| | | | |
|---|---|---|---|
| 6,456,721 B1 | 9/2002 | Fukuda |
| 6,463,157 B1 | 10/2002 | May |
| 7,010,139 B1 | 5/2006 | Smeehuyzen |
| 7,532,934 B2 | 5/2009 | Lee |
| 7,716,988 B2 | 5/2010 | Ariav |
| 7,749,154 B2 | 7/2010 | Cornel |
| 7,789,837 B2 | 9/2010 | Lehrman |
| 7,866,212 B2 | 1/2011 | Ariav |
| 8,024,044 B2 | 9/2011 | Kirby |
| 8,346,354 B2 | 1/2013 | Hyde |

(Continued)

FOREIGN PATENT DOCUMENTS

| | | |
|---|---|---|
| CN | 201361029 A | 1/2009 |
| CN | 104188638 A | 12/2014 |

(Continued)

OTHER PUBLICATIONS

Pevernagie D., Aarts R.M., De Meyer M.: The acoustics of snoring. Sleep Medicine Review 14(2010) 131-144.

(Continued)

*Primary Examiner* — Keri J Nelson

(57) ABSTRACT

The present invention provides an apparatus and methods to deliver audible acoustic sound to the brain through bone conduction and to terminate snoring and sleep apnea. The apparatus comprises a control module and a device that measures signs of the snoring and the sleep apnea and generates the audible acoustic sound to arouse a subject. The device is reversibly attachable to a part of a head overlying a skull of the subject and uses a composite sensor comprising a reflectance pulse oximeter and a vibration sensor for the measurement and an acoustic speaker for generation of the sound. The device drives the acoustic speaker to produce human-conversational sound and non-human sound.

6 Claims, 7 Drawing Sheets

(56) References Cited

U.S. PATENT DOCUMENTS

| | | |
|---|---|---|
| 8,374,701 B2 | 2/2013 | Hyde |
| 8,482,418 B1 | 7/2013 | Harman |
| 8,577,464 B2 | 11/2013 | Mashiach |
| 8,579,794 B2 | 11/2013 | Henke |
| 8,588,906 B2 | 11/2013 | Ternes |
| 8,588,930 B2 | 11/2013 | DiUbaldi |
| 8,591,430 B2 | 11/2013 | Amurthur |
| 8,630,712 B2 | 1/2014 | Moses |
| 8,639,313 B2 | 1/2014 | Westbrook |
| 8,639,343 B2 | 1/2014 | De Vos |
| 8,655,441 B2 | 2/2014 | Fletcher |
| 8,771,204 B2 | 7/2014 | Telfort |
| 8,781,587 B2 | 7/2014 | Alt |
| 8,808,158 B2 | 8/2014 | Harrison |
| 8,823,490 B2 | 9/2014 | Libbus |
| 8,823,753 B2 | 9/2014 | Kim et al. |
| 8,862,196 B2 | 10/2014 | Lynn |
| 8,892,205 B2 | 11/2014 | Miller, III |
| 8,934,970 B2 | 1/2015 | Ternes |
| 9,028,429 B2 | 5/2015 | Telfort |
| 9,050,024 B2 | 6/2015 | Ujhazy |
| 9,072,613 B2 | 7/2015 | Shantha |
| 9,092,965 B2 | 7/2015 | Lyons |
| 9,114,256 B2 | 8/2015 | El Achhab |
| 2004/0197002 A1 | 10/2004 | Atsumi |
| 2006/0018488 A1 | 1/2006 | Viala |
| 2008/0308112 A1 | 12/2008 | Aarts |
| 2009/0060231 A1 | 3/2009 | Buroojy |
| 2010/0069773 A1 | 3/2010 | Henke |
| 2010/0076251 A1 | 3/2010 | Stasz |
| 2010/0076252 A1 | 3/2010 | Henke |
| 2010/0249677 A1 | 9/2010 | DiUbaldi |
| 2010/0274070 A1 | 10/2010 | Moses |
| 2011/0172552 A1 | 7/2011 | Rothman |
| 2011/0274309 A1* | 11/2011 | Doh ............... H04R 9/047 381/398 |
| 2013/0281883 A1 | 10/2013 | Nishida |
| 2013/0331662 A1 | 12/2013 | Stoian |
| 2014/0010387 A1 | 1/2014 | Cohen |
| 2014/0051938 A1 | 2/2014 | Goldstein |
| 2015/0073232 A1 | 3/2015 | Ahmad |
| 2015/0142075 A1 | 3/2015 | Miller, III |
| 2015/0173672 A1 | 6/2015 | Goldstein |
| 2015/0224018 A1 | 8/2015 | Graindorge |

FOREIGN PATENT DOCUMENTS

| | | |
|---|---|---|
| JP | 2005237807 A | 9/2005 |
| JP | 2005349167 A | 12/2005 |

OTHER PUBLICATIONS

Anton Coenen: Subconscious stimulus recognition and processing during sleep. Psyche vol. 16. Issue 2 (2010).

McAlonan K., Brown V.J., Bowman E.M.: Thalamic Reticular Nucleus Activation Reflects Attentional Gating during Classical Conditioning. Journal of Neuroscience 2000, 20(23):8897-8901.

* cited by examiner

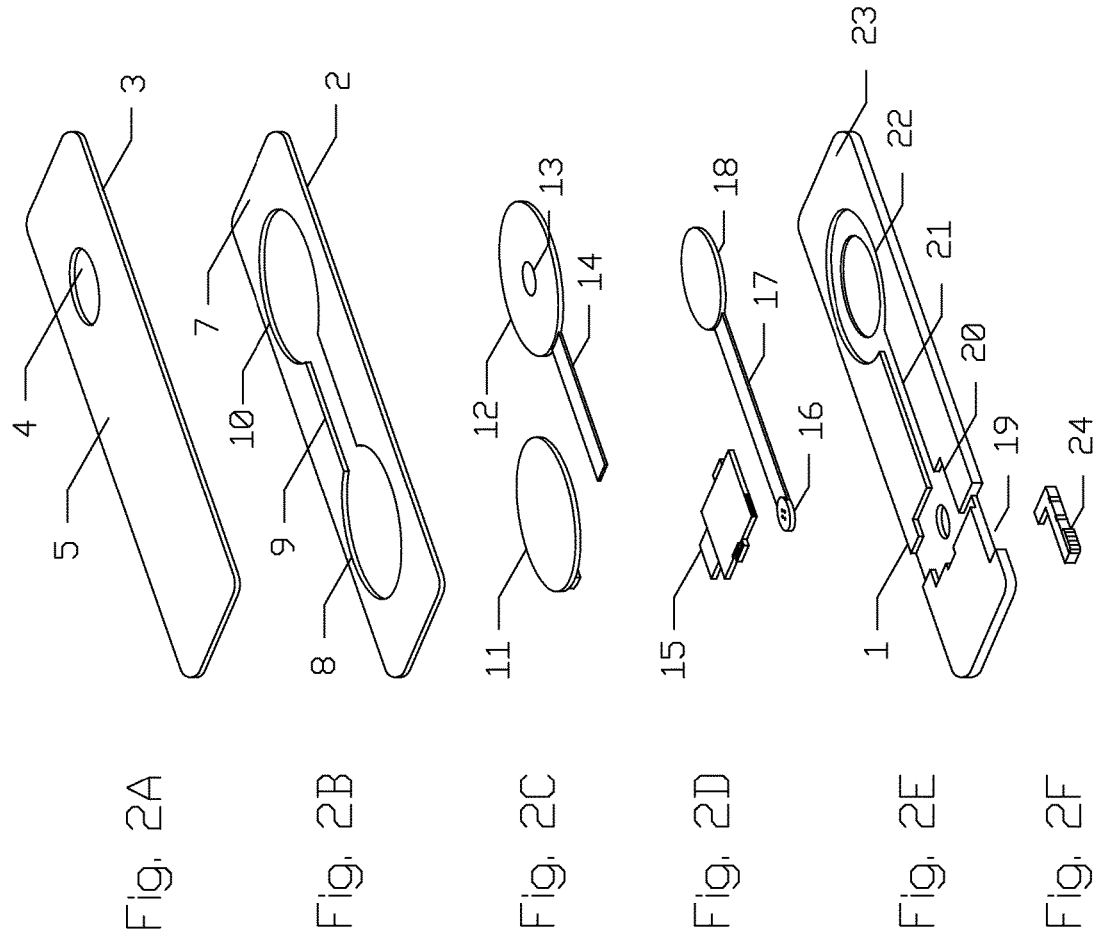

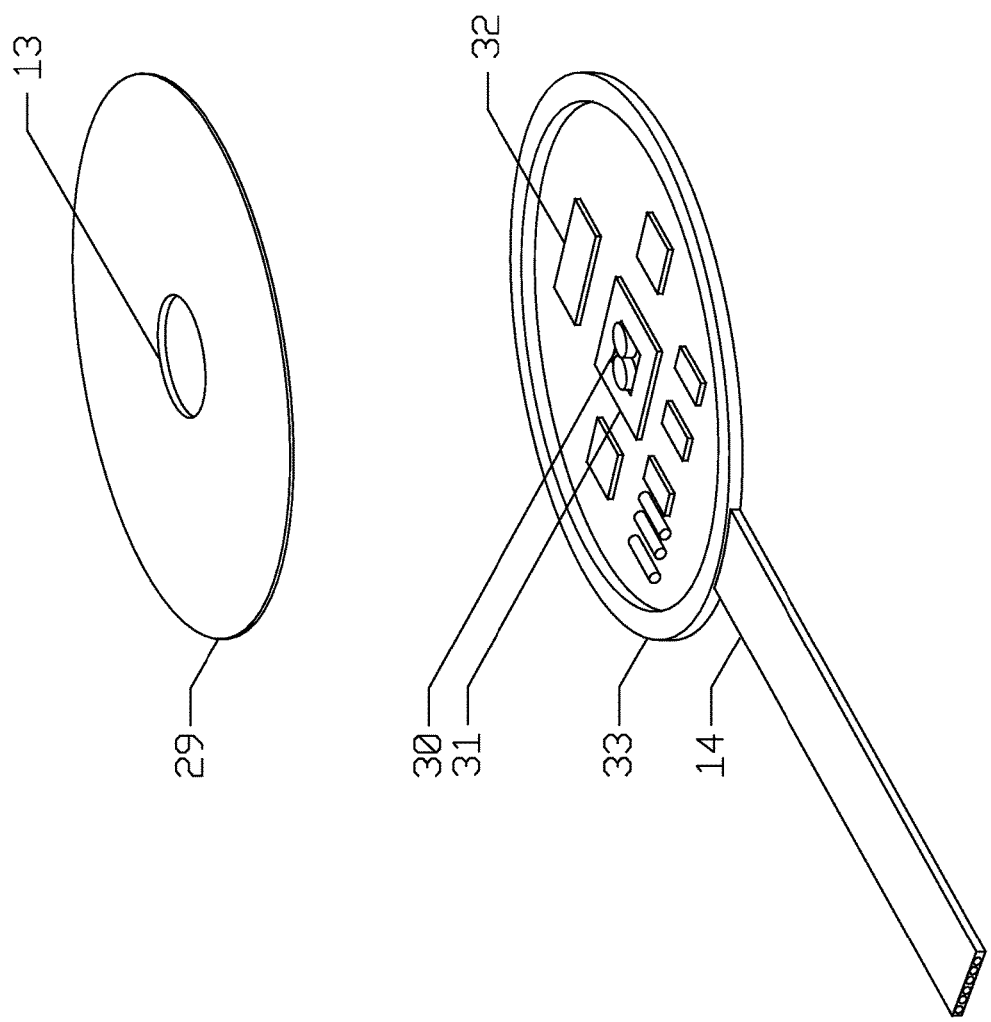

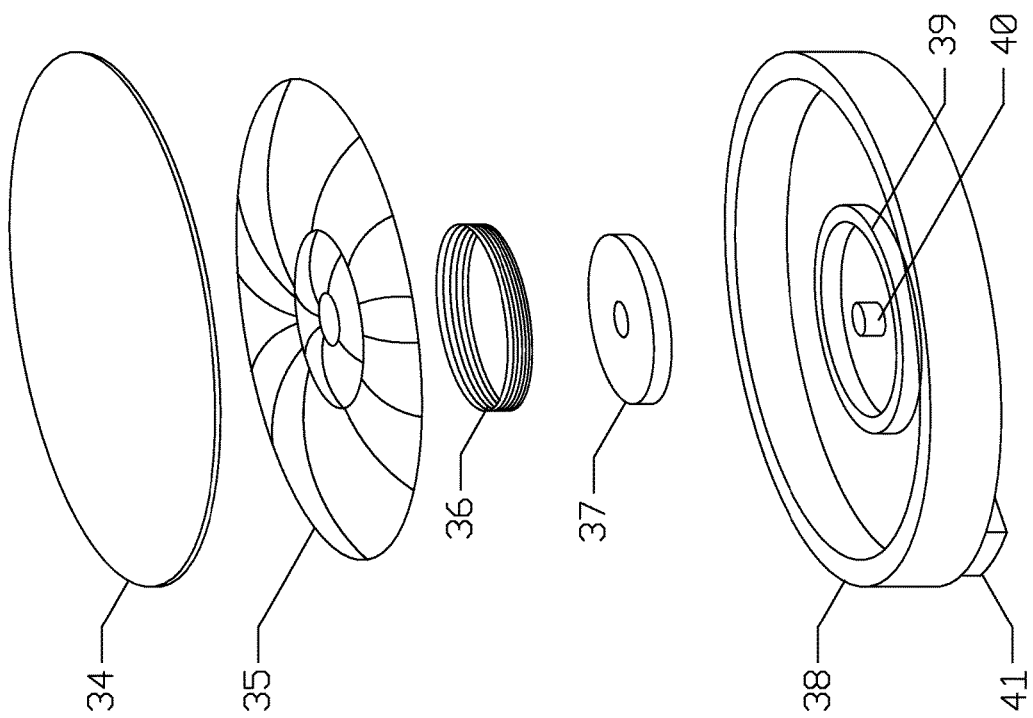
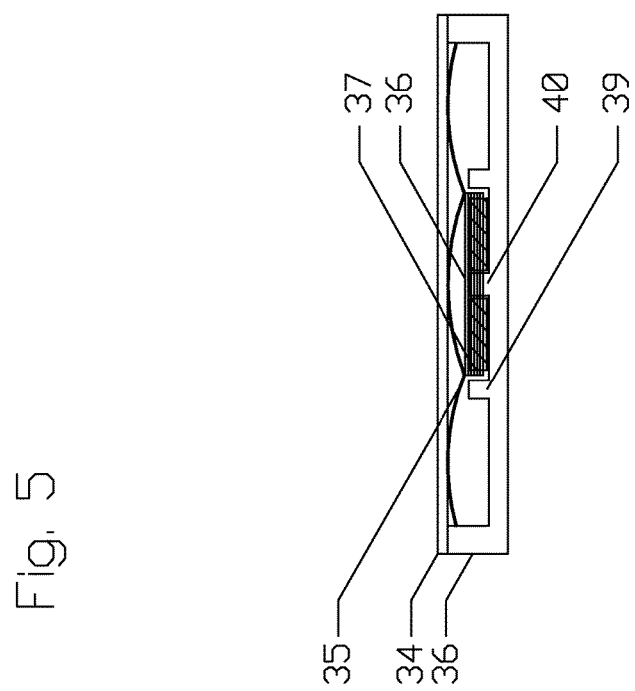
Fig. 5

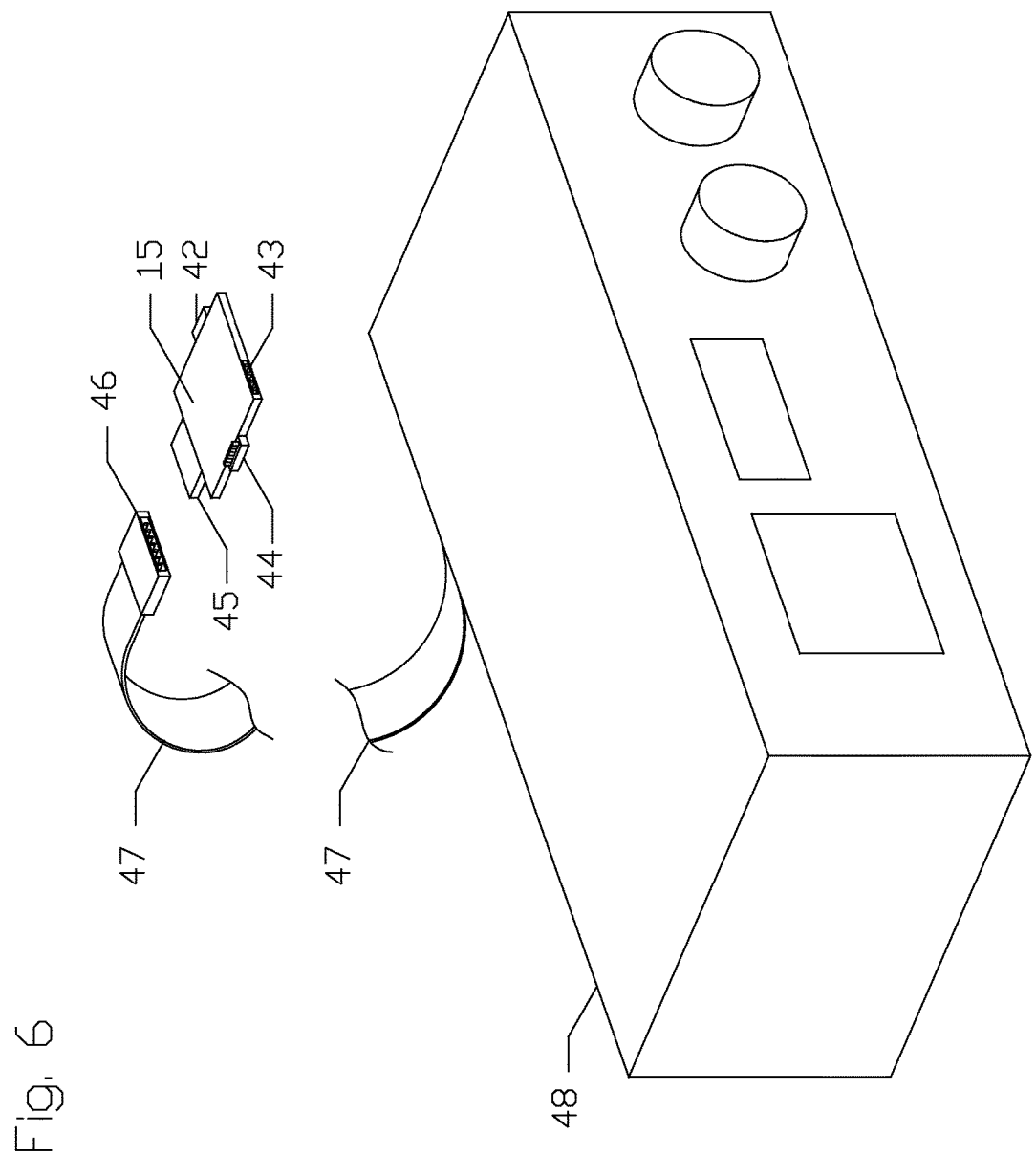

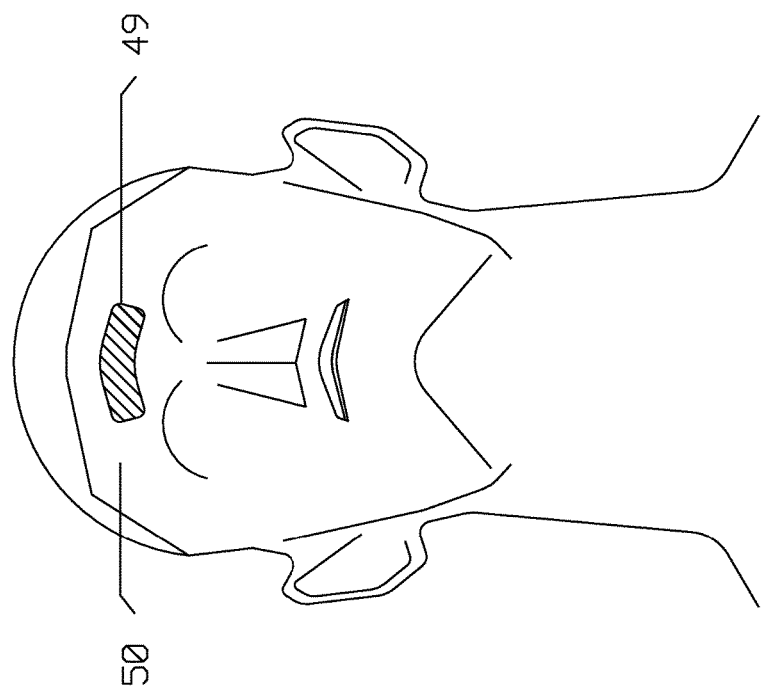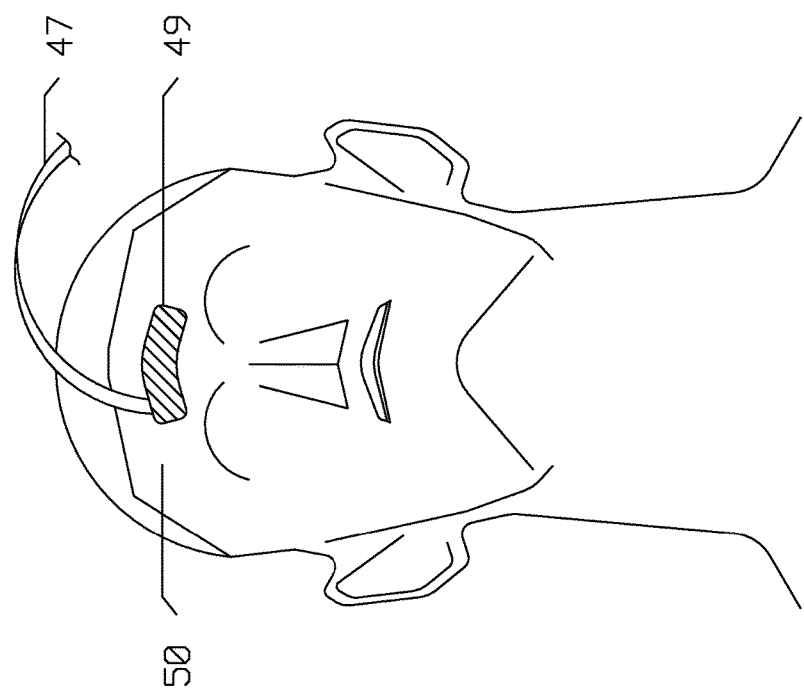

US 10,076,280 B2

BONE-CONDUCTIVE AROUSAL INDUCTION APPARATUS

TECHNICAL FIELD

The present invention relates generally to the field of terminating snoring and sleep apnea. More specifically, the present invention provides an apparatus and methods to acoustically stimulate the brain through bone conduction of sound to a cochlear nerve to alter stages of sleep associated with the snoring and the sleep apnea.

BACKGROUND OF THE INVENTION

Human respiration is governed by two systems of the brain, with one system located in the brain stem autonomously controlling involuntary contraction and relaxation of both the intercostal muscles and diaphragm, and the other in the cerebral cortex consciously controlling voluntary respiration. Oxygen level and pH balance over a functionally safe range in blood and tissue of human beings are autonomously maintained by lungs driven by the system in the brain stem whereas the system in the cerebral cortex can consciously alter the status of respiration without affecting vital function of the body dependent on the oxygenation and the pH balance. Kidneys also participate in maintaining the pH balance by reclaiming bicarbonate back to blood in case exhaling capacity of the lungs is exceeded to remove excess carbonic acid from blood. The conscious control of the respiration by the cerebral cortex not only affects frequency and depth of the contraction and relaxation of both the intercostal muscles and diaphragm but also utilizes voluntary muscles in pharynx, larynx and tongue. The voluntary muscles in the pharynx, larynx and tongue, together with associated involuntary muscles of these organs, form an inlet of airway for the lungs and help protect the lungs for autonomous gas exchange function.

Although disorders of the brain stem comprising medulla oblongata and pons are known to be responsible for well-recognized abnormalities of breathing such as Cheyene-Stokes respiration, these events are rare, occurring only in seriously ill patients who are likely hospitalized for terminal disorders. Consequently patients with the brain stem disorders require specially trained physicians and nurses who would need to rely on sophisticated equipments such as a ventilator to sustain life of the patients. On the other hand, there are a significantly larger number of people who have problems in the voluntary respiration while relatively functioning well for daily activities out in communities. These problems range from a simple snoring to significant obstructive sleep apnea, which occur during sleep but improve upon arousal and awakening. There are several well-identified causes for these problems, and it is presumed that one common denominator for these is an insufficient air intake across the inlet surrounded by the voluntary muscles of the pharynx, larynx and tongue. Loss of contractile muscle tone of the voluntary muscles and narrowing of the inlet by anatomical abnormalities have been attributed as most common causes of the problems and as such the mainstay of corrective measures for the problems has been to force air across the narrowed inlet into the lungs. This, the continuous positive airway pressure (CPAP) breathing, has been continuously improved in its methodology and equipment, yet it fundamentally requires a mask to fit to a mouth/nose of a patient while sleeping. Despite the limitation, the CPAP breathing has been accepted by the majority as the standard therapy of choice for the problems of voluntary breathing, based on its benign and effective noninvasive management and widespread acceptance by patients.

The loss of muscle tone of voluntary respiratory muscles is coincided with deepening stages of sleep that is known to reversibly reduce voluntary responses of an individual to external sensory stimuli. This process is believed to be mediated by blocking a portion of the thalamus that controls flow of external sensor stimuli to the cerebral cortex. Once the individual arouses or awakes, the cerebral cortex begins resuming activity that provides necessary muscle tone for the voluntary respiratory muscles, thereby maintaining a patient airway inlet. According to several studies, this thalamic-gating during sleep, however, is not complete but the brain is yet responsive to subconscious stimuli having a meaning to the individual or signaling danger from the environment (Coenen, 2010). For an example, sleeping subjects arose faster with spiking K complexes on EEG when hearing their own names than on hearing other names (Oswald, Taylor & Treisman, 1960). One study showed that sleeping subjects who were motivated to awake by presenting a specific stimulus awoke easier on these stimuli than non-motivated subjects (Zung & Wilson, 1961). Another study utilizing auditory stimuli and simultaneous recording of both EEG and fMRI in sleeping humans showed that parts of prefrontal cortex were more activated by stimuli having a specific significance than by neutral stimuli (Portas et al, 2000).

Auditory stimuli can be delivered through a cochlear (acoustic) branch of the vestibulo-cochlear nerve to the brain. The cochlear nerve receives auditory stimuli from a tympanic membrane in the ear canal and from bones surrounding the cochlear nerve structure. Efficiency of transmission of vibration in audible frequency is known to be better through bone conduction to the cochlear nerve than through air conduction via the tympanic membrane. This dual mode of transmission of vibration in audible frequency through the cochlear nerve allows fail-safe reception of external acoustic stimuli by the auditory complex of the brain.

Snoring comes from vibration of the airway inlet in the audible range of vibration, usually around 500 Hz in frequency, which is transmitted to soft tissue and bony structure of a skull of an individual. Snoring can be classified as primary snoring and secondary snoring. The primary snoring comes from palatal vibration at a frequency range of 20 Hz to 500 Hz whereas the secondary snoring is associated with sleep apnea occurring from non-palatal structure at a frequency of 500 Hz to 2000 Hz with a median around 1000 Hz (Pevernagie et al, 2008). People with the primary snoring continue to take in oxygen in a way they do not develop a significant drop in their oxygen saturation level in blood and tissue. In contrast, patients with an obstructive sleep apnea and the secondary snoring have a sequence of a short-lived initial snoring followed by a temporary blockade of the airway inlet by collapsing soft tissues and voluntary muscles of the throat to a point that there is no air movement across the blocked airway inlet multiple times during sleep. People with a moderate to severe sleep apnea are known to have ≥15 episodes of no breathing lasting 10 seconds or longer each night. Their brain generally does not wake them up in time before a significant drop in blood and tissue oxygen oftentimes to less than 90% of oxygen saturation (Crummy et al, 2007). In this instance, there won't be measurable vibrations from the airway inlet following the initial high pitch snoring until the patients become profoundly hypoxic.

Invasive-device-based management of a medical condition requires a careful risk-benefit evaluation, especially for its long-term implication of interactions with a human body. Over the past few years, there has been a great interest in direct electric stimulation of the nerves governing voluntary muscles of the airway inlet such as the hypoglossal nerve. Although it appears logical in an electromechanical engineering sense, there are significant flaws in this approach. Firstly, there has to be a solid establishment of a causal relationship between the snoring/obstructive sleep apnea and dysfunctioning cranial nerves, if there is any, including hypoglossal nerves. Additional gain of an increase in neuronal stimulation of the voluntary muscles of the airway inlet by the electrical stimulation may not be quantitatively significant when the cranial nerves are already functioning normal on their own, unless intensity of electrical neuronal stimulation exceeds a steady-state threshold of muscle contraction that on its own has no abnormal pathology to get corrected for. Secondly, we do not know a long-term outcome of electrically-stimulated cranial nerves, except that clinical study can only answer the long-term outcome regarding benefit, side effects and complications of the invasive placement of an electric device on or around cranial nerves. It is conceivable that there would be a range of risk involved in daily electric stimulation of cranial nerves since unlike electric cables, human nerve fibers are living cells which require constant renewal and maintenance at a molecular level. Damages to the nerves such as apoptotic death or atrophy of nerve cells, if occurred, may become permanent or semi-permanent for the majority of large trunk nerve fibers. It would take many years to study safety issues regarding functionality and viability of the electrically stimulated cranial nerves. Thirdly, it would be a hard sell for invasive placement of an electric stimulation device to people who have a mild to moderate obstructive sleep apnea that can be successfully managed by the CPAP breathing which is noninvasive.

There are devices which are to sense vibration of snoring/obstructive sleep apnea and to provide an individual with external stimuli including auditory stimuli to arouse the individual. Focusing only on measurable vibration of the airway inlet would miss occasions of cessation of breathing in case of complete apnea resulting in hypoxia of the individual since there would not be air movement across the airway inlet. For patients with a moderate to severe obstructive sleep apnea, the devices detecting vibration as a source of input data for generating external stimuli to the patients would not be able to help them avoid hypoxic conditions during episodes of apnea. In other instances, devices using air conduction to deliver external acoustic stimuli to the cochlear nerve requires an ear piece like an earphone an individual needs to wear during sleep. Issues of comfort with the earphone stuck in ear canals every night inevitably become an issue of compliance. Furthermore, the obstructive sleep apnea is more prevalent in older people who tend to develop decrease in hearing oftentimes due to conditions related to reduced air conduction of hearing such as disorders of the middle ear and ossification of the conduction apparatus in the middle ear.

To overcome these limitations, the present invention proposes that both the vibration of the airway inlet and decrease in tissue oxygen saturation be non-invasively detected as a source of input data for generating external acoustic stimuli to an individual, that the external acoustic stimuli be delivered through the bone conduction to the cochlear nerve, and that the external acoustic stimuli be relevant and specific to the individual to achieve high efficiency of the external acoustic stimulation to temporarily arouse the individual from a deep stage of sleep to a lighter stage of sleep at a time the airway inlet collapses due to relaxation of the voluntary muscles of the airway inlet. Preferably, initial set-up of the present invention would be done in a sleep laboratory that can monitor arousal responses and changes in snoring/apnea/hypoxia of an individual to various acoustic stimuli. Once a particular set of acoustic stimuli is chosen, it can be downloaded in a flash memory part of the present invention that works autonomously once activated.

Any repetitive stimuli to the brain are known to induce conditioned reflex that can wear off by increasing a threshold of response to the repetitive stimuli. This process may translate into a progressive loss of the arousal response to prolonged stimulation by the acoustic stimuli, thereby decreasing efficiency. In addition, direct exposure of the brain to adjacent electromagnetic radiation and radiofrequency waves emitting from any electrical devices is known to detrimental, although exact types of abnormal pathology related to a particular electromagnetic radiation or radiofrequency waves are not well established. The present invention proposes that arousal responses to stimuli be recorded for assessment of efficiency and that the brain of a user be shielded from radiofrequency waves generated by the present invention.

SUMMARY OF THE INVENTION

To achieve the goals of detecting both vibration of the airway inlet and tissue hypoxia, the present invention combines a vibration sensor with a reflectance pulse oximeter in a single unit. For bone conduction of acoustic stimuli that make sense to a user, the present invention uses a planar diaphragm moving-coil speaker that is in direct contact with a part of a head overlying a skull. Both the planar diaphragm moving-coil speaker and a composite sensor of the vibration sensor and the reflectance pulse oximeter are housed in a thin flexible enclosure that is shielded and reversibly attachable to a part of a head overlying a skull. The enclosure also houses a battery, a processing circuit assembly, and a connecting outlet to a separate control module. The control module is configured to monitor input data from the composite sensor, to modulate the acoustic stimuli and to download an electronic information for acoustic stimulation to the processing circuit assembly.

In one embodiment, the bone-conductive arousal induction apparatus comprises two devices which are reversibly connectable to each other. One of the devices is the control module and the other device is an input and output device that is to be reversibly attached to a subject's skin around the head. The control module is configured to receive the input data from the composite sensor of the input and output device, to correlate the input data to episodes of snoring/sleep apnea/hypoxia and to send an electronic output to the input and output device. The input and output device is configured to be reversibly attached to a part of a head overlying a skull, to pick up vibration signal transmitted from the airway inlet to the part of the head overlying the skull, to periodically measure tissue oxygen saturation of a soft tissue covering the part of the head overlying the skull, to send both the vibration signal and tissue oxygen saturation data to the processing circuit assembly of the input and output device, to produce on-demand audible acoustic sound from the planar diaphragm moving coil speaker of the input and output device and to transmit the audible acoustic sound to a bony structure of the skull via a soft tissue of the head overlying the skull. The audible acoustic sound is transmitted to and perceived by the cochlear nerve endings located in the inner ear.

In one embodiment, the input and output device comprises the battery as power source, the processing circuit assembly, the connecting outlets, the composite sensor of the vibration sensor and the reflectance pulse oximeter and the planar diaphragm moving coil speaker and is assembled in a multi-layered flat rectangular panel which is pliably deformable along a longitudinal axis of the input and output device. The input and output device comprises at least three layers of the flat rectangular panel, with an inner panel facing a skin of the part of the head overlying the skull such as forehead, an outer panel covering components of the input and output device and a mid panel housing the components in carved-out enclosures inside the mid panel. A lower surface of the inner panel is configured to be reversibly and securely attachable to the skin and an upper surface of the inner panel covers a lower surface of the mid panel. The mid panel has at least two carved-out enclosures located in tandem along the longitudinal axis. One enclosure houses the planar diaphragm moving coil speaker and the other enclosure houses the composite sensor. A planar diaphragm of the planar diaphragm moving coil speaker faces the upper surface of the inner panel. The composite sensor is housed in a separate enclosure located opposite to the planar diaphragm moving coil speaker enclosure. The reflectance pulse oximeter of the composite sensor faces the skin of the part of the head overlying the skull through an aperture made in one part of the inner panel. The processing circuit assembly, configured in a flat panel comprising at least microprocessors, a flash memory and the internal controller, is located in between the planar diaphragm moving coil speaker and a lower surface of the outer panel. The battery is located in between the composite sensor and the lower surface of the outer panel. The upper surface of the inner panel and the lower surface of the upper panel are covered with a metallic ink comprising particulated metal such as copper or aluminum to shield radiofrequency waves generated from electronic components of the input and output device to a level below 0.0001 $\mu W/cm^2$ to a soft tissue of a human body.

In one embodiment, the input and output device of the bone-conductive arousal induction apparatus is configured to function autonomously without electrical and electronic connection, including wireless electronic connection, with the control module. The autonomous function is to be activated and deactivated by a switch attached to the input and out device. The autonomous function is supported by the battery as power source which drives the processing circuit assembly, the composite sensor of the vibration sensor and the reflectance pulse oximeter and the planar diaphragm moving coil speaker. The processing circuit assembly is configured to process the input data of the vibration and the oxygen saturation, and to initiate, maintain and terminate various electronic signals to the planar diaphragm moving coil speaker to produce audible acoustic sound. The processing circuit assembly also is configured to drive the reflectance pulse oximeter.

In one embodiment, both the vibration sensor and reflectance pulse oximeter of the composite sensor are assembled on one printed circuit board. The composite sensor has a flat planar configuration and fixedly housed in a single enclosure. The reflectance pulse oximeter comprises a red light emitting diode and an infrared light emitting diode located right next to the red light emitting diode, and a plurality of photodiodes surrounding both diodes. Both the red and infrared light emitting diodes and the photodiodes face the skin of the part of the head overlying the skull through the aperture located in the inner panel of the input and output device. The composite sensor is electrically connected to the processing circuit assembly that receives voltage data of the photodiodes of the reflectance pulse oximeter correlated to tissue oxygen saturation and data generated from the vibration sensor upon sensing vibrations. A main component of the vibration sensor comprises an inertial MEMS (microelectromechanical system) accelerometer such as ADXL 335 (Analog Devices, Inc).

In one embodiment, the processing circuit assembly is configured to receive and convert an analogue input from the composite sensor to a digitized set of data for analysis by the microprocessor and for storage in the flash memory of the processing circuit assembly, to send the digitized set of data to the control module when connected to the control module and to activate/deactivate the planar diaphragm moving coil speaker via the internal controller of the processing circuit assembly based on a predefined set of commands stored in the flash memory when working autonomously without connection to the control module. The flash memory is configured to store a set of commands for the processing circuit assembly, the composite sensor and the planar diaphragm moving coil speaker and for communication with the control module and to store a digitized, chronological set of input data from the composite sensor. The flash memory is also configured to be capable for receiving downloads from the control module and for uploading the digitized set of input data to the control module.

In one embodiment, a command from either the flash memory or the control module for activating the planar diaphragm moving coil speaker is to be triggered by the input data from the reflectance pulse oximeter of the composite sensor below a set of thresholds of tissue oxygen saturation. The threshold of the present invention for a tissue oxygen saturation for people not having a lung disease is 90% below which the planar diaphragm moving coil speaker is to be activated. The threshold for a tissue oxygen saturation for patients with a lung disorder of a less than one month duration is 90%. The threshold for a tissue oxygen saturation for patients with a known chronic lung disorder such as chronic obstructive pulmonary disorder (COPD) is a drop of more than 5% below the average oxygen saturation at rest of a particular patient.

In one embodiment, the command from either the flash memory or the control module for activating the planar diaphragm moving coil speaker is to be triggered by the input data from the vibration sensor of the composite sensor above a set of thresholds of vibration. The threshold for a triggerable episode of vibration for people with the primary snoring without an underlying lung disorder is successive vibrations lasting at least 20 seconds in frequencies between 20 Hz and 500 Hz. The threshold for a triggerable episode of vibration for people with the primary snoring with a lung disorder including both an acute lung disorder of less than one month duration or a chronic lung disorder such as COPD is successive vibrations lasting at least 10 seconds in frequencies between 20 Hz and 500 Hz. The threshold for the triggerable episode of vibration for people with the secondary snoring associated with sleep apnea, whether there is a lung disorder or not, is successive vibrations lasting at least 10 seconds in frequencies between 500 Hz and 2000 Hz.

In one embodiment, the activation of the planar diaphragm moving coil speaker is triggered by the input data from either the reflectance pulse oximeter or the vibration sensor of the composite sensor. Duration of arousal of a subject is configured to be adjustable by the control module to less than 15 seconds upon each activation of the planar diaphragm moving coil speaker. This can be accomplished by varying intensity of sound pressure from 5 dB to 60 dB, by varying duration of activation of the planar diaphragm moving coil speaker and/or by varying contents of sound, by the control module. In an ideal setting, the subject will undergo an initial evaluation for testing the arousal by the present invention in a sleep laboratory. Once the most ideal set of commands for the arousal are sorted out by the control module for the subject to achieve an arousal response lasting less than 15 seconds while avoiding an awakening response which makes the subject aroused for more than 15 seconds, these commands are then downloaded to the flash memory of the input and output device the subject can use at home without the control module.

In one embodiment, the commands from either the control module or the flash memory of the input and output device are configured to produce human-conversational sound from the planar diaphragm moving coil speaker. for an example, the human-conversational sound that has a meaning to a subject may include calling name of a subject such as 'John~', alerting words such as 'Watch out' or 'Wake up', or greeting words such as 'Hi', which can be objectively assessed for development of K complexes on EEG during a sleep study. Other example of the meaningful human-conversational sound may include short phrases such as 'Breathe deep'. Another example of the meaningful human-conversational sound may include short sentences such as 'You need to breathe'.

In other embodiment, the commands from either the control module or the flash memory of the input and output device are configured to produce non-human sound that signals a danger such as a beeping sound, which can also be objectively assessed for the development of K complexes on EEG during a sleep study. Intensity of the non-human sound is configured to range from 5 dB to 60 dB and duration of the non-human sound is configured to vary, which is to achieve an arousal lasting less than 15 seconds. The commands from either the control module or the flash memory of the input and output device also are configured to sequentially produce both the human-conversational sound and the non-human sound in one set of activation of the planar diaphragm moving coil speaker.

In one embodiment, the reflectance pulse oximeter receives commands from either the control module or the flash memory of the input and output device to check on a tissue oxygen saturation of a soft tissue of head of a subject on a regular basis. For people with the primary snoring not having a lung disease, the reflectance pulse oximeter checks on the tissue oxygen saturation only at the time snoring occurs. For people with the primary snoring having a lung disease whether it is an acute or a chronic disease, the reflectance pulse oximeter is configured to start checking on the tissue oxygen saturation at the time snoring starts and then to continue checking at a regular interval, for an example, every five minutes, until the tissue oxygen saturation improves above 92% for the people with an acute lung disease or above the average tissue oxygen saturation at rest for the people with a chronic lung disorder such as COPD. For a patient with the secondary snoring having a mild lung disease, the reflectance pulse oximeter is configured to start checking on the tissue oxygen saturation at the time snoring starts and then to continue checking at a regular interval, for an example, every five minutes, until the tissue oxygen saturation improves above the average tissue oxygen saturation at rest of the patient. For a patient with the secondary snoring having a moderate to severe lung disease with significant hypoxia, the reflectance pulse oximeter is configured to start checking on the tissue oxygen saturation at a pre-determined time during sleep even without snoring, for an example, an hour after going to the bed, and then to continue checking at a regular interval, for an example, every fifteen minutes, until the patient wakes up and turns off the input and output device.

In one embodiment, the input and output device has a means to turn on either only the vibration sensor for a group of subjects with the primary snoring as the only problem, which simplifies electronic algorithms and saves battery power, or both the vibration sensor and the reflectance pulse oximeter for other groups having the primary snoring and lung diseases or the secondary snoring. The vibration sensor of the composite sensor is configured to be on once the input and output device is turned on and to be active until the input and output device is turned off. Sensitivity of the vibration sensor is adjustable by the control module to reduce occasions of false positive readings and to increase rate of detection of true positive events of snoring.

BRIEF DESCRIPTION OF THE DRAWINGS

FIGS. 2A, 2B, 2C, 2D, 2E and 2F show a schematic exploded view of individual components of the input and output device: FIG. 2A represents a lower panel with an aperture; FIG. 2B shows a mid panel with two separate carved-out enclosures and a connecting planar conduit; FIG. 2C shows a planar diaphragm moving coil speaker and a composite sensor; FIG. 2D shows a processing circuit assembly and a battery; FIG. 2E shows an upper panel with carved-out portions corresponding to internal components; FIG. 2F shows a switch that turns on and off the input and output device.

FIG. 3A represents an off-position of the switch; FIG. 3B shows an on-position of the switch to turn on the input and output device with simultaneous activation of a vibration sensor and a reflectance pulse oximeter of the composite sensor; FIG. 3C shows an on-position of the switch to turn on the input and output device with only the vibration sensor being activated.

FIG. 4 depicts a schematic layout of the composite sensor.

FIG. 5 shows a schematic illustration of the planar diaphragm moving coil speaker: FIG. 5A shows a profile view and FIG. 5B shows an exploded view of components.

FIG. 6 shows a schematic drawing of the processing circuit assembly of the input and output device and a separate control module.

FIGS. 7A and 7B show schematic examples of application of the input and output device on a forehead of a subject: FIG. 7A depicts the input and output device connected to the control module via a connecting cable; FIG. 7B illustrates the input and output device applied to the forehead without connection to the control module.

DETAILED DESCRIPTION OF THE DRAWINGS

As described below, the present invention provides an arousal induction apparatus through bone conduction and methods of use. It is to be understood that the descriptions are solely for the purposes of illustrating the present invention, and should not be understood in any way as restrictive or limited. Embodiments of the present invention are preferably depicted with reference to FIGS. 1 to 7, however, such reference is not intended to limit the present invention in any manner. The drawings do not represent actual dimension of devices, but illustrate the principles of the present invention.

Figure 1:
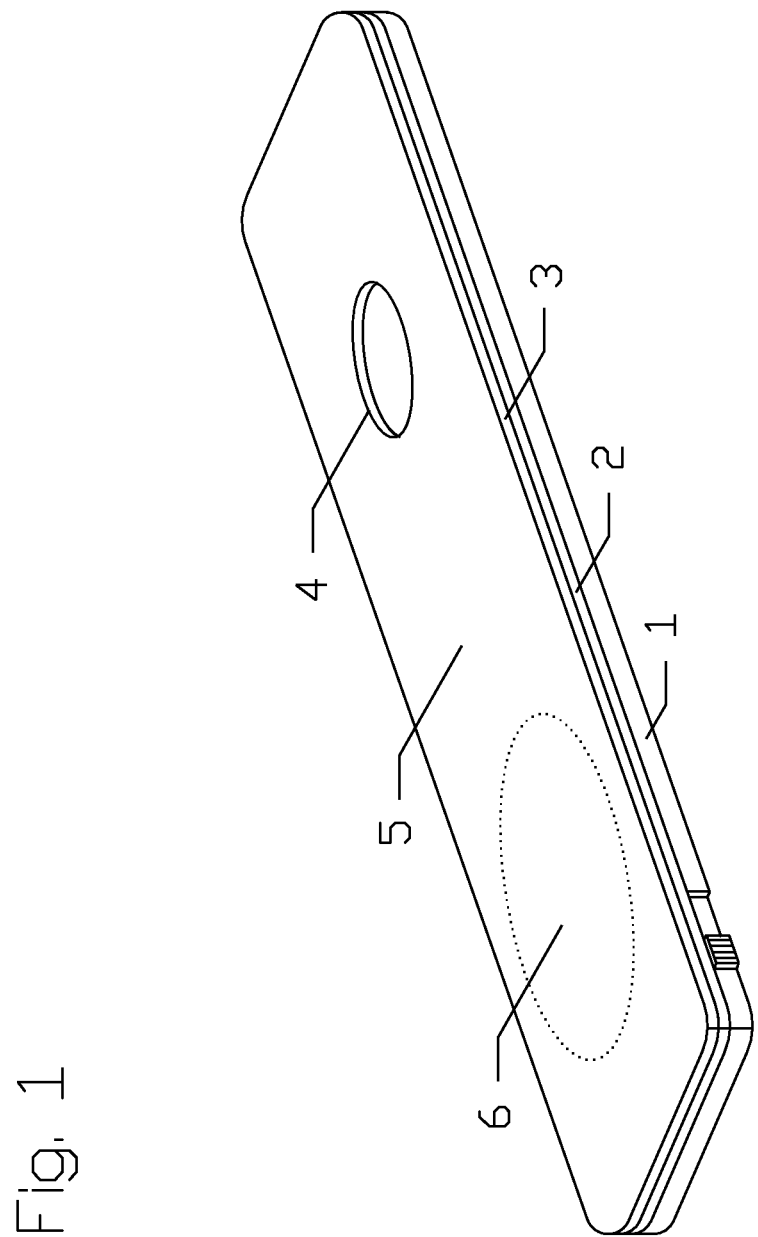
FIG. 1 shows a schematic presentation of an input and output device of the present invention.

FIG. 1 shows a schematic presentation of an input and output device of the present invention. The input and output device is configured in a thin flexible multi-layered rectangular panel. The multi-layered rectangular panel comprises an upper panel 1, a mid panel 2 and a lower panel 3, with each panel tightly attached to the other panel. On a lower surface 5 of the lower panel 3, there is provided an aperture 4 through which light passes from an oximeter housed in the mid panel 2. On the other portion of the lower surface 5, there is provided an area 6 for transmitting acoustic sound from a planar diaphragm moving coil speaker housed in the mid panel 2. The lower surface 5 is configured to be reversibly attachable to a skin of a subject by such means as adhesives applied on the lower surface 5.

FIGS. 2A, 2B, 2C, 2D, 2E and 2F show a schematic exploded view of individual components of the input and output device. FIG. 2A represents the lower panel 3 with the aperture 4 and the lower surface 5. An upper surface of the lower panel 3 is treated with a metallic ink containing a particulated metal such as copper or aluminum to block off radiofrequency from components of the input and output device. FIG. 2B shows the mid panel 2 that has a lower surface 7, two separate carved-out enclosures 8 and 9 and a connecting planar conduit 9. The lower surface 7 is tightly attached to an upper surface of the lower panel 3. FIG. 2C shows the planar diaphragm moving coil speaker 11 and a composite sensor 12 with a central hole 13 in a central portion of the composite sensor 12 facing the lower panel 3 of FIG. 2A. The composite sensor 12 is configured to be connected to a processing circuit assembly via a electric band cable 14. The planar diaphragm moving coil speaker 11 is to be housed in the enclosure 8 of FIG. 2B and the composite sensor 12 is to be housed in the enclosure 10 of FIG. 2B. The electric band cable 14 is to be inserted in the connecting conduit 9 of FIG. 2B. FIG. 2D shows the processing circuit assembly 15 and a battery 18. The battery 18 provides the input and output device with an electric power through a connecting band cable 17 and an electric connecting port 16 which is hooked up to a corresponding port of the processing circuit assembly 15. The processing circuit assembly 15 distributes and regulates the electric power to the processing circuit assembly 15, the planar diaphragm moving coil speaker 11 and the composite sensor 12. FIG. 2E shows the upper panel 1 with a lower surface 23 that is tightly attached to an upper surface of the mid panel 2. The lower surface 23 of the upper panel 1 is treated with the metallic ink containing the particulated metal such as copper or aluminum to block off radiofrequency from components of the input and output device. The upper panel 1 has carved-out portions 19~22 corresponding to internal components: a switch recess 19 for a switch 24 of FIG. 2F; an enclosure 20 for the processing circuit assembly 15 of FIG. 2D; a connecting conduit 21 for the connecting band cable 17 of FIG. 2D; an enclosure 22 to house the battery 18 of FIG. 2D and a part of the composite sensor 12 of FIG. 2C. FIG. 2F shows the switch 24 that turns on and off the input and output device.

Figure 3A:
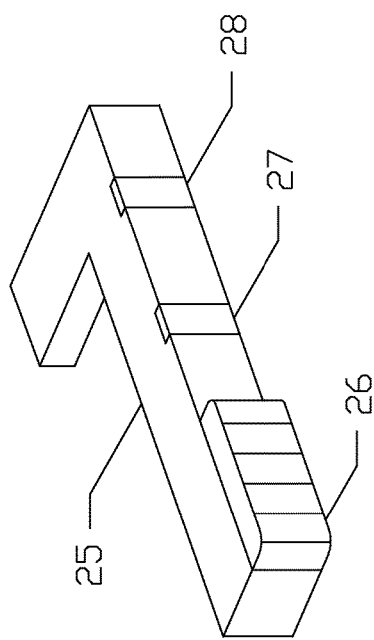
FIGS. 3A, 3B and 3C illustrate configurations of the switch.
Figure 3B:
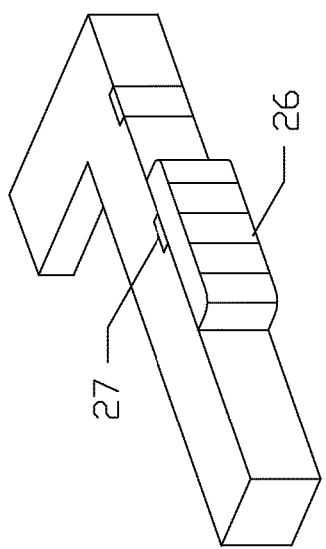
Figure 3C:
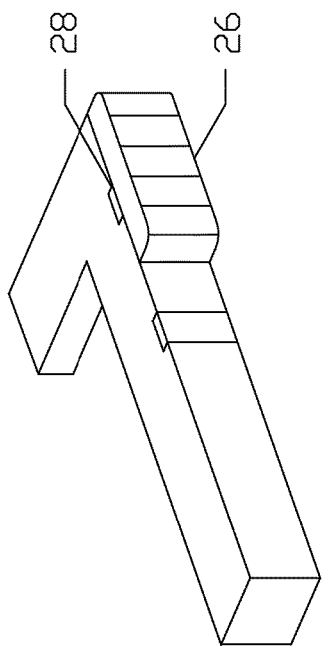

FIGS. 3A, 3B and 3C illustrate configurations of the switch. FIG. 3A represents an off-position of the switch, showing a main body 25, a slidable knob 26, a first contact electrode 27, a second contact electrode 28 of the switch. FIG. 3B shows an on-position of the switch with the slidable knob 26 contacting the first contact electrode 27, which is to turn on the input and output device with simultaneous activation of a vibration sensor and a reflectance pulse oximeter of the composite sensor 12 of FIG. 2C. FIG. 3C shows an on-position of the switch with the slidable knob 26 contacting the second contact electrode 28, which is to turn on the input and output device with only the vibration sensor of the composite sensor 12 of FIG. 2C being activated.

Components of the composite sensor 12 of FIG. 2C are shown in FIG. 4, which comprises a thin top cover 29 having the central hole 13, a printed circuit board 33 with an outer rim, a pair of light emitting diodes 30 surrounded by an array of photodiodes 31 of the reflectance pulse oximeter, the vibration sensor 32 and the electric band cable 14. The top cover 29 fixedly covers the printed circuit board 33 to seal off inner components and is treated with the metallic ink containing the particulated metal such as copper or aluminum to block off radiofrequency waves generated from the composite sensor. The light emitting diodes 30 emit red and infrared lights to a tissue of a subject through the hole 13 and the photodiodes 31 receives reflected light coming from the tissue through the hole 13 for measuring tissue oxygen saturation. The electric band cable 14 is flexible.

FIG. 5 shows a schematic illustration of the planar diaphragm moving coil speaker. A profile view of the speaker in FIG. 5A shows a sound-transmitting top cover 34, an enclosure 38 housing a planar diaphragm 35, a moving coil 36 and a magnet 37 inserted in a magnet guide 39 having a central rod 40 to centrally position the magnet 37 inside the magnet guide 39. The exploded view of FIG. 5B shows the top cover 34, the planar diaphragm 35, the moving coil 36, the magnet 37, the enclosure 38, the magnet guide 39 with the central rod 40. There is provided an electric connecting pin arrangement 41 that connects the planar diaphragm moving coil speaker to the processing circuit assembly 15 of FIG. 2D. An inner surface of both the top cover 34 and enclosure 38 is treated with the metallic ink containing the particulated metal such as copper or aluminum to block off radiofrequency from the components of the planar diaphragm moving coil speaker. Upon electric activation, the moving coil 36 vibrates around the magnet 37, which is transmitted to the planar diaphragm 35 to generate audible acoustic sound.

FIG. 6 shows a schematic drawing of the processing circuit assembly 15 of the input and output device and a separate control module 48. The processing circuit assembly 15 has a few electric connecting pin ports 42-45; the pin port 42 is to get connected with a pin arrangement of the electric band cable 14 of FIG. 4; the pin port 43 is to get connected with the switch 24 of FIG. 2F; the pint port 44 is to get connected with the pin arrangement 41 of the planar diaphragm moving coil speaker of FIG. 5; the pin port 45 is to get connected with a pin arrangement 46 of an electric band cable 47 of the control module 48. The processing circuit assembly 15 receives an analogue electric information of both oxygen saturation data and vibration data from the composite sensor 12, converts it to a digitized electronic information and sends it to the control module 48. The control module 48 analyzes and compares the digitized information to a predefined set of threshold criteria of activation of the planar diaphragm moving coil speaker 11 of FIG. 2C. The control module 48 then sends a set of commands, once the threshold criteria of activation is met, to the processing circuit assembly 15 that in turn activates the planar diaphragm moving coil speaker 11. The processing circuit assembly not only activates the planar diaphragm moving coil speaker upon the commands from the control module but also retains the set of commands in a flash memory part of the processing circuit assembly for an autonomous activation when the input and output device is turned on without connection with the control module.

FIGS. 7A and 7B show schematic examples of reversible application of the input and output device 49 on a forehead 50 of a subject for management of snoring, sleep apnea and hypoxia occurring during sleep. FIG. 7A depicts the input and output device 49 connected to the control module via the electric cable 47, which is a typical arrangement for use in a sleep laboratory where the control module can be monitored and operated by a trained individual. FIG. 7B illustrates the input and output device 49 applied to the forehead 50 without connection to the control module, for a typical home use of the input and output device by the subject once the initial setup has been completed by the trained individual of the sleep laboratory using the control module.

It is to be understood that the aforementioned description of the apparatus and methods is simple illustrative embodiments of the principles of the present invention. Various modifications and variations of the description of the present invention are expected to occur to those skilled in the art without departing from the spirit and scope of the present invention. Therefore the present invention is to be defined not by the aforementioned description but instead by the spirit and scope of the following claims.

What is claimed is:

1. A bone-conductive arousal induction apparatus, comprising an input and output device, and a control module, wherein the input and output device is provided in a relatively broad surface in relation to thickness and configured to be reversibly attachable to a skin of a head overlying a skull of a subject, wherein the input and output device comprises a multi-layered flexible rectangular panel, a composite sensor to gather information on tissue oxygen saturation and tissue vibration of the subject, a planar diaphragm moving coil speaker to produce audible acoustic sound, a processing circuit assembly and a battery as power source, wherein the input and output device is configured either to be operated by the control module or to operate autonomously, and wherein the input and output device is configured to arouse the subject from a stage of sleep by transmitting the audible acoustic sound to a cochlear nerve of the subject via bone conduction of the sound through the skull; the control module, provided as a separate device from the input and output device and configured to be connectable to the input and output device, wherein the control module receives and stores the information on the tissue oxygenation and the tissue vibration of the subject, wherein the control module has a set of action threshold criteria of the tissue oxygen saturation and the tissue vibration to activate the planar diaphragm moving coil speaker of the input and output device, wherein the control module has electronic commands for initiation and termination of periodic monitoring the tissue oxygen saturation, and wherein the control module sends and uploads a set of electronic commands to the processing circuit assembly of the input and output device to activate the planar diaphragm moving coil speaker, wherein the input and output device comprises:

the multi-layered flexible rectangular panel, provided in at least three layers of the rectangular panel with each layer tightly attached to the other layers, wherein the multi-layered flexible rectangular panel houses internal components of the input and output device, wherein the multi-layered flexible rectangular panel has an aperture on a panel contacting the skin to let light pass through to and from the composite sensor, and wherein the multi-layered flexible rectangular panel is treated with a metallic ink to shield a tissue from radiofrequency waves generated by the input and output device to a level below 0.0001 $\mu W/cm^2$;

the composite sensor, provided in a single printed circuit board, wherein the composite sensor comprises a reflectance pulse oximeter and an inertial microelectromechanical system accelerometer, and wherein the composite sensor measures and sends data of the tissue oxygen saturation and the tissue vibration to the processing circuit assembly of the input and output device;

the planar diaphragm moving coil speaker, wherein the planar diaphragm moving coil speaker is configured to generate the audible acoustic sound with a sound pressure ranging from 5 dB to 60 dB;

the processing circuit assembly, provided in a single printed circuit board, wherein the processing circuit assembly comprises microprocessors, a flash memory and an internal controller, wherein the processing circuit assembly receives, processes and sends the data of the tissue oxygen saturation and the tissue vibration to the control module, wherein the processing circuit assembly receives and stores the set of the electronic commands from the control module to activate the planar diaphragm moving coil speaker of the input and output device, and wherein the processing circuit assembly is configured to operate autonomously when disconnected from the control module; and the battery, wherein the battery provides the input and output device with electric power for autonomous operation of the input and output device.

2. A hone-conductive arousal induction apparatus, comprising an input and output device, and a control module, wherein the input and output device is provided in a relatively broad surface in relation to thickness and configured to be reversibly attachable to a skin of a head overlying a skull of a subject, wherein the input and output device comprises a multi-layered flexible rectangular panel, a composite sensor to gather information on tissue oxygen saturation and tissue vibration of the subject, a planar diaphragm moving coil speaker to produce audible acoustic sound, a processing circuit assembly and a battery as power source, wherein the input and output device is configured either to be operated by the control module or to operate autonomously, and wherein the input and output device is configured to arouse the subject from a stage of sleep by transmitting the audible acoustic sound to a cochlear nerve of the subject via bone conduction of the sound through the skull; the control module, provided as a separate device from the input and output device and configured to be connectable to the input and output device, wherein the control module receives and stores the information on the tissue oxygenation and the tissue vibration of the subject, wherein the control module has a set of action threshold criteria of the tissue oxygen saturation and the tissue vibration to activate the planar diaphragm moving coil speaker of the input and output device, wherein the control module has electronic commands for initiation and termination of periodic monitoring the tissue oxygen saturation, and wherein the control module sends and uploads a set of electronic commands to the processing circuit assembly of the input and output device to activate the planar diaphragm moving coil speaker, wherein the set of action threshold criteria of the tissue oxygen saturation to activate the planar diaphragm moving coil speaker of the input and output device comprises:

the tissue oxygen saturation of 90% or below for people without a lung disorder and for patients with an acute lung disorder of a less than one month duration; and the tissue oxygen saturation of a drop of more than 5% below an average oxygen saturation at rest for patients with a chronic lung disorder.

3. A bone-conductive arousal induction apparatus, comprising an input and output device, and a control module, wherein the input and output device is provided in a relatively broad surface in relation to thickness and configured to be reversibly attachable to a skin of a head overlying a skull of a subject, wherein the input and output device comprises a multi-layered flexible rectangular panel, a composite sensor to gather information on tissue oxygen saturation and tissue vibration of the subject, a planar diaphragm moving coil speaker to produce audible acoustic sound, a processing circuit assembly and a battery as power source, wherein the input and output device is configured either to be operated by the control module or to operate autonomously, and wherein the input and output device is configured to arouse the subject from a stage of sleep by transmitting the audible acoustic sound to a cochlear nerve of the subject via bone conduction of the sound through the skull; the control module, provided as a separate device from the input and output device and configured to be connectable to the input and output device, wherein the control module receives and stores the information on the tissue oxygenation and the tissue vibration of the subject, wherein the control module has a set of action threshold criteria of the tissue oxygen saturation and the tissue vibration to activate the planar diaphragm moving coil speaker of the input and output device, wherein the control module has electronic commands for initiation and termination of periodic monitoring the tissue oxygen saturation, and wherein the control module sends and uploads a set of electronic commands to the processing circuit assembly of the input and output device to activate the planar diaphragm moving coil speaker, wherein the set of action threshold criteria of the tissue vibration to activate the planar diaphragm moving coil speaker of the input and output device comprises:

successive vibrations lasting at least 20 seconds in frequencies between 20 Hz and 500 Hz for people with a primary snoring without an underlying lung disorder;

successive vibrations lasting at least 10 seconds in frequencies between 20 Hz and 500 Hz for people with the primary snoring with a lung disorder; and successive vibrations lasting at least 10 seconds in frequencies between 501 Hz and 2000 Hz for people with a secondary snoring associated with sleep apnea.

4. A method of arousing the subject by the bone-conductive arousal induction apparatus, comprising an input and output device, and a control module, wherein the input and output device is provided in a relatively broad surface in relation to thickness and configured to be reversibly attachable to a skin of a head overlying a skull of a subject, wherein the input and output device comprises a multi-layered flexible rectangular panel, a composite sensor to gather information on tissue oxygen saturation and tissue vibration of the subject, a planar diaphragm moving coil speaker to produce audible acoustic sound, a processing circuit assembly and a battery as power source, wherein the input and output device is configured either to be operated by the control module or to operate autonomously, and wherein the input and output device is configured to arouse the subject from a stage of sleep by transmitting the audible acoustic sound to a cochlear nerve of the subject via bone conduction of the sound through the skull; the control module, provided as a separate device from the input and output device and configured to be connectable to the input and output device, wherein the control module receives and stores the information on the tissue oxygenation and the tissue vibration of the subject, wherein the control module has a set of action threshold criteria of the tissue oxygen saturation and the tissue vibration to activate the planar diaphragm moving coil speaker of the input and output device, wherein the control module has electronic commands for initiation and termination of periodic monitoring the tissue oxygen saturation, and wherein the control module sends and uploads a set of electronic commands to the processing circuit assembly of the input and output device to activate the planar diaphragm moving coil speaker, wherein duration of an arousal response of the subject to the audible acoustic sound transmitted to the cochlear nerve via bone conduction of the sound through the skull is limited to less than 15 seconds per each arousal, adjusted by varying intensity of the sound pressure from 5 dB to 60 dB, by varying duration of activation of the planar diaphragm moving coil speaker and by varying contents of the audible acoustic sound.

5. A method of monitoring the tissue oxygen saturation by the bone-conductive arousal induction apparatus, comprising an input and output device, and a control module, wherein the input and output device is provided in a relatively broad surface in relation to thickness and configured to be reversibly attachable to a skin of a head overlying a skull of a subject, wherein the input and output device comprises a multi-layered flexible rectangular panel, a composite sensor to gather information on tissue oxygen saturation and tissue vibration of the subject, a planar diaphragm moving coil speaker to produce audible acoustic sound, a processing circuit assembly and a battery as power source, wherein the input and output device is configured either to be operated by the control module or to operate autonomously, and wherein the input and output device is configured to arouse the subject from a stage of sleep by transmitting the audible acoustic sound to a cochlear nerve of the subject via bone conduction of the sound through the skull; the control module, provided as a separate device from the input and output device and configured to be connectable to the input and output device, wherein the control module receives and stores the information on the tissue oxygenation and the tissue vibration of the subject, wherein the control module has a set of action threshold criteria of the tissue oxygen saturation and the tissue vibration to activate the planar diaphragm moving coil speaker of the input and output device, wherein the control module has electronic commands for initiation and termination of periodic monitoring the tissue oxygen saturation, and wherein the control module sends and uploads a set of electronic commands to the processing circuit assembly of the input and output device to activate the planar diaphragm moving coil speaker, wherein the monitoring of the tissue oxygen saturation starts:

at a time a snoring during sleep occurs for people with the primary snoring;

at a time the snoring during sleep occurs for patients with the secondary snoring having a mild lung disease; and at a pre-determined time during sleep for patients with the secondary snoring having a moderate to severe lung disease.

6. A method of monitoring the tissue oxygen saturation by the bone-conductive arousal induction apparatus, comprising an input and output device, and a control module, wherein the input and output device is provided in a relatively broad surface in relation to thickness and configured to be reversibly attachable to a skin of a head overlying a skull of a subject, wherein the input and output device comprises a multi-layered flexible rectangular panel, a composite sensor to gather information on tissue oxygen saturation and tissue vibration of the subject, a planar diaphragm moving coil speaker to produce audible acoustic sound, a processing circuit assembly and a battery as power source, wherein the input and output device is configured either to be operated by the control module or to operate autonomously, and wherein the input and output device is configured to arouse the subject from a stage of sleep by transmitting the audible acoustic sound to a cochlear nerve of the subject via bone conduction of the sound through the skull; the control module, provided as a separate device from the input and output device and configured to be connectable to the input and output device, wherein the control module receives and stores the information on the tissue oxygenation and the tissue vibration of the subject, wherein the control module has a set of action threshold criteria of the tissue oxygen saturation and the tissue vibration to activate the planar diaphragm moving coil speaker of the input and output device, wherein the control module has electronic commands for initiation and termination of periodic monitoring the tissue oxygen saturation, and wherein the control module sends and uploads a set of electronic commands to the processing circuit assembly of the input and output device to activate the planar diaphragm moving coil speaker, wherein the monitoring of the tissue oxygen saturation terminates:

at a time the snoring during sleep is terminated for the people with the primary snoring;

at a time the tissue oxygen saturation improves above 92% for the people with the primary snoring having the acute lung disease;

at a time the tissue oxygen saturation improves above the average oxygen saturation at rest for the people with the primary snoring having the chronic lung disorder;

at a time the tissue oxygen saturation improves above the average oxygen saturation at rest for the people with the secondary snoring having the mild lung disorder; and at a time patients wake up for the patients with the secondary snoring having the moderate to severe lung disorder.

* * * * *